United States Patent [19]
Kulkarni et al.

[11] Patent Number: 6,025,446
[45] Date of Patent: Feb. 15, 2000

[54] STABLE COMPLEXES OF CROSSLINKED POLYVINYLPYRROLIDONE AND IODINE AND METHOD OF MAKING THE SAME

[76] Inventors: Arun B. Kulkarni, 1 Eric La., East Brunswick, N.J. 08816; Gregory R. Skover, 60 Cedar La., Princeton, N.J. 08540

[21] Appl. No.: 09/028,388

[22] Filed: Feb. 24, 1998

Related U.S. Application Data

[63] Continuation of application No. 08/783,807, Jan. 16, 1997, which is a continuation of application No. 08/487,260, Jun. 7, 1995, abandoned.

[51] Int. Cl.[7] ........................................... C08F 8/22
[52] U.S. Cl. ........................................ 525/326.9; 525/356
[58] Field of Search ............................................ 525/326.9

[56] References Cited

U.S. PATENT DOCUMENTS

| | | | |
|---|---|---|---|
| 3,671,545 | 6/1972 | Halpern | 525/326.9 |
| 4,027,083 | 5/1977 | Herrle et al. | 525/326.9 |
| 5,242,985 | 9/1993 | Shih et al. | 525/326.9 |

*Primary Examiner*—Bernard Lipman
*Attorney, Agent, or Firm*—Lawrence D. Schuler; Ruby T. Hope

[57] ABSTRACT

A wound treatment material which absorbs wound fluid without overdrying the wound, provides physical cushioning for the wound, and releases an antimicrobial agent (iodine) in a controlled manner to kill harmful micro-organisms without irritating the wound area or adversely affecting would healing. The wound treatment material comprises crosslinked polyvinylpyrrolidone-iodine complex which is water insoluble, but water-absorbent and water-swellable. When the complex or a wound treatment preparation containing the complex is applied to a wound, i.e., becomes hydrated, and an equilibrium is established between the complex and the wound at the wound/complex interface. Iodine is releaed from the crosslinked polyvinylpyrrolidone-iodine complex by a diffusion controlled process which responds to the reduction in concentration of free iodine in the wound fluid in equilibrium with the complex. The greater the rate of iodine depletion in the wound, the greater the rate of iodine release from the polymer-iodine complex. It has been discovered that this diffusion controlled release mechanism can be utilized to deliver antimicrobially effective amounts of iodine to the wound while maintaining the concentration of iodine below the concentration that could cause significant wound irritation or retardation of healing. It has also been found that the moist environment at the wound/complex interface and the physical protective effect (cushioning) offered by the hydrated complex can enhance wound healing.

6 Claims, 1 Drawing Sheet

Key:
A. Conventional povidone-iodine solution
B. Composition according to US Patent No. 5,242,985 (Shih, et al)
C. Composition according to this invention

STABLE COMPLEXES OF CROSSLINKED POLYVINYLPYRROLIDONE AND IODINE AND METHOD OF MAKING THE SAME

This is a continuation of application Ser. No. 08/783,807 filed Jan. 16, 1997, which is a continuation of application Ser. No. 08/487,260, filed Jun. 7, 1995, both now abandoned.

BACKGROUND OF THE INVENTION

1. Field of the Invention

This invention is directed to an antimicrobial material which can be applied to minor wounds, cuts, abrasions and burns for the prevention of infections and for the promotion of rapid healing. More particularly, the invention relates to complexes of polyvinylpyrrolidone (PVP) and iodine. Even more particularly, the invention relates to complexes of crosslinked polyvinylpyrrolidone and iodine capable of providing effective antimicrobial activity while at the same time avoiding wound irritation and retardation of wound healing. The invention also includes a method for preparing such complexes of crosslinked PVP and iodine. The invention further includes preparations, such as powders, gels and the like, which contain such complexes.

2. Description of Prior Art

Current antiseptic products are generally quite effective in reducing microbial counts in vitro, although many of them suffer from limitations inherent in their antimicrobial spectra and are readily inactivated by wound fluid/serum. Another major drawback of currently used antiseptic agents is the relative balance between their antimicrobial efficacy and their cytotoxic potential. When used in concentrations that exhibit adequate antimicrobial activity, they are generally irritating to wounds to varying degrees and/or retard wound healing significantly. Conversely, when used in concentrations which minimize or avoid irritation of wounds or retardation of wound healing, they either do not have sufficient antimicrobial activity in the first instance or their antimicrobial activity quickly dissipates to inadequate levels.

Topical antimicrobial materials and preparations containing them have long been recognized as important parts of disinfection of intact skin and/or wounds. Antimicrobial materials used for this purpose represent a wide variety of chemical compositions including phenols, halogens, peroxides, quaternary ammonium compounds and antibiotics. These antimicrobial agents vary greatly in their effectiveness against different types of micro-organisms to which the skin or wound might be exposed. They also vary greatly in terms of their susceptibility to inactivation by contact with blood, serum or wound fluid as well as changes in pH or ionic environment. Many antimicrobial agents that show a wide effective range of biocidal activity are used for disinfection of inanimate objects such as hard surfaces and instruments but cannot be effectively used on skin or particularly on wounds because of the lack of wide differentiation between their biocidal effects on micro-organisms versus mammalian tissues.

Iodine has long been recognized as an antimicrobial agent with outstanding effectiveness against a wide range of micro-organisms including Gram positive and Gram negative bacteria, mycobacteria, fungi, protozoa and viruses. It remains effective over a wide pH range and, unlike a large majority of other antimicrobial agents, it is not readily inactivated by proteins in the wound fluid/serum. Iodine readily penetrates microbial cell walls and is believed to exert its biocidal activity through a number of interactions including the following:

1) Oxidation of sulfhydryl groups in enzymes and proteins;
2) Inactivation by iodination of phenolic groups in amino acids and proteins;
3) Iodination of basic -NH- groups in amino acids and nucleotides that serve as critical hydrogen bonding sites;
4) Iodination of unsaturated lipids/fatty acids leading to membrane immobilization.

As used in the art, the term "available iodine" refers to any form of iodine that has oxidizing capacity. Such forms are titratable with sodium thiosulfate and include elemental iodine, triiodide ion, hypoiodite ion, and iodate ion.

In a typical aqueous iodine solution, e.g., a solution containing 2% w/v iodine ($I_2$) and 2.4% w/v sodium iodide (NaI), the available iodine exists in several species in equilibrium with each other. These species include elemental iodine ($I_2$), hypoiodic acid (HOI), hypoiodite ion ($OI^-$), hydrated iodine cation ($H_2OI^+$), iodate ion $[IO_3]^-$ and triiodide ion $[I_3]^-$. Most antiseptic formulations, and the aqueous environment of wounds to which they are applied, have a pH range of 3 to 9. In this pH range of 3 to 9, the concentrations of hydrated iodine cation, hypoiodite ion, and iodate ion are so low that they can be essentially neglected. Tri-iodide ion readily dissociates into elemental iodine and iodide ion in highly diluted solution. Thus, the primary active species in highly diluted aqueous iodine solution are elemental iodine i.e., $I_2$, and hypoiodic acid, i.e., HOI, in equilibrium. The relative proportions of the two species depends on the pH and the available iodine content. Concentrations of free iodine as low as 0.5 to 2 ppm exhibit antimicrobial effect. The term "free iodine" refers to available iodine which is not bound to another chemical substance such as a polymer or surfactant.

Tincture of iodine, which is a hydro-alcoholic solution of elemental iodine ($I_2$) and sodium iodide (NaI), is well recognized as a degerming antiseptic and has been in use for presurgical prepping of skin for over one hundred years. However, it is highly irritating, corrosive and toxic when in contact with a body cavity, mucus membranes or wounds. It also has other undesirable side effects that make it unsuitable for wound treatment. These include potential for occasional hypersensitivity reactions, skin staining and unpleasant odor.

Major advances in utilizing the antimicrobial efficacy of iodine while minimizing its tissue toxicity and other undesirable side effects were made with the advent of iodophors. Iodophors are readily dissociable, loose complexes of triiodide or iodine with polymers or surfactants. Iodophors not only increase the solubility of iodine in aqueous media but reduce its chemical potential and vapor pressure, thereby reducing its undesirable side effects. The iodophors serve as reservoirs of iodine and function by slowly releasing iodine at the site of application. A well known and very widely used iodophor is polyvinylpyrrolidone-iodine complex, which is also known as PVP-iodine. Since the term "Povidone" is an art recognized synonym for polyvinylpyrrolidone, it will be understood that the term "Povidone-iodine" is synonymous with, and an alternative way of referring to, a polyvinylpyrrolidone-iodine complex. Its available iodine content ranges between 9% and 12%. Spectroscopic studies by Schenck et al., reported in Structure of polyvinylpyrrolidone-iodine, J. Pharm. Sci., 68, p 1505–1509, 1979, indicate that Povidone-iodine consists of adjacent pyrrolidone units complexed with hydrogen triiodide rather than elemental iodine. Therefore, only two thirds of its entire iodine content constitutes available iodine. One third of the entire iodine in this complex is in the unavailable iodide form.

Povidone-iodine is utilized in commercially available disinfectant products such as Betadine® and Isodine® that are widely used in hospitals for prepping of skin prior to surgery and as surgical scrubs and hand washes for health care personnel hand washes.

Although they are useful for application to intact skin, iodophor solutions as well as most other topically effective antimicrobial preparations based on quaternary ammonium salts or chlorhexidine salts are not well suited for use on wounds. In these preparations, all of the antimicrobially active content is in solution and in direct contact with the wound. Furthermore, in order to be effective over an extended period of time, the concentrations of the active agents far exceed minimum inhibitory concentrations by several orders of magnitude. At these concentrations, the active agents exert cytotoxic, cytopathic or cytostatic effects on the wound tissue as well as on cells, such as fibroblasts, involved in the wound repair process. As a result, the wound repair process is significantly and undesirably retarded.

Lineaweaver et al., Topical antimicrobial toxicity; Arch. Surgery, 120, p 267–270, 1985, found in human fibroblast tissue culture studies that no fibroblasts survived 24 hours after a 15 minute exposure to 1% povidone-iodine, 3% hydrogen peroxide or 0.5% sodium hypochlorite. These studies also showed that the cytotoxicity threshold concentration of soluble povidone-iodine was below 0.01% and above 0.001%. It was also found that re-epithelialization of full thickness dermal wounds on the backs of rats was substantially and statistically significantly inhibited at eight days after initial irrigation with 1% povidone-iodine or with 0.5% sodium hypochlorite.

Rosso, in U.S. Pat. No. 4,323,557, describes adhesives containing N-vinylpyrrolidone in the polymer backbone. In these adhesives, iodine complexing, monomeric units of vinylpyrrolidone are co-polymerized with other adhesive co-monomers. Therefore, the iodine complexing N-vinylpyrrolidone units in this polymeric adhesive are rendered water-insoluble. Pressure sensitive films with such adhesives can be complexed with iodine for providing its slow release. These compositions can be used as antimicrobial surgical drapes. However, they cannot be used on wound surface due to the risk of physical reinjury to the healing wound tissues from direct contact with the adhesive.

Shih, in U.S. Pat. No. 5,242,985, describes a complex of a strongly swellable, moderately crosslinked polyvinylpyrrolidone and iodine. The composition is capable of releasing iodine substantially uniformly over a 6 hour period in the presence of water. Shih's complex is prepared by a method which employs a particular type of crosslinked polyvinylpyrrolidone described in his earlier U.S. Pat. No. 5,073,614. Shih defines narrower ranges for its characteristics (aqueous gel volume, Brookfield viscosity and crosslinker concentration) required for the iodine complex. Shih's iodine complexes are prepared by moistening the specific powdered crosslinked polyvinylpyrrolidone with a small amount of isopropanol or isopropanol/water mixture, mixing the moistened crosslinked polyvinylpyrrolidone with approximately 20%, based on the weight of the PVP polymer of iodine at room temperature, and then heating it at 45° C. for 2 hours and then at 90° c. for 16 hours. The resulting PVP/iodine complex is a light yellow, free flowing fine powder containing approximately 10% available iodine and approximately 5% iodide. The Shih complex releases its available iodine at a uniform rate over a six hour period. In view of this uniform rate of release, the concentration of soluble, available iodine at the wound site will exceed cytotoxic levels within a relatively short period of time, e.g., a few hours, after application of the Shih complex to a wound. This means that use of the Shih material will, at some point in time, undesirably result in wound irritation and/or retardation of wound healing. Those skilled in the art will also notice that nearly one fourth of the iodine used in the preparation of the complex described by Shih et al is unaccounted for and another one fourth is reduced to iodide. This strongly indicates that the starting polymer, i.e., crosslinked polyvinylpyrrolidone, is partially oxidized by iodine during the preparation of the complex under the processing conditions used for iodination. Without wishing to be bound by any particular theory, it is thought that this partial oxidation may account for the observed uniform release pattern of available iodine into the aqueous environment. Although the compositions described in Shih's U.S. Pat. No. 5,242,985 may expose wounds to lower initial iodine levels compared to conventional povidone-iodine, this lower initial level is expected to last for a relatively short time and, as indicated above, cytotoxic levels can be expected to be reached within a few hours.

SUMMARY OF THE INVENTION

It has now been unexpectedly found that a stable, water-insoluble and water-swellable crosslinked polyvinylpyrrolidone-iodine complex prepared by an iodination process which differs from that disclosed by Shih in U.S. Pat. No. 5,242,985 is capable of providing effective antimicrobial action on skin and wounds while at the same time avoiding wound irritation and retardation of wound healing. It has been further unexpectedly found that compositions containing the complex of the present invention actually promote wound healing, possibly by supplementing its non-cytotoxic nature with physical protection/cushioning and moist/non-desiccating environment offered by the hydrated and swollen polymer.

The crosslinked polyvinylpyrrolidone-iodine complex of the present invention is water-insoluble but water-swellable and is capable of releasing iodine in an equilibrium controlled diffusion process which depends on the concentration of free iodine in the wound fluid to which the complex is applied. The concentration of free iodine in contact with the wound is maintained below the cytotoxic potential which irritates the wound and significantly retards the healing process. When this polymer complex comes in contact with the wound fluid, it becomes hydrated, swells and permits iodine to diffuse from the complex into the wound. As the concentration of the available iodine in the wound fluid increases at the wound complex interface, the rate of release of iodine is reduced until an equilibrium is reached between the iodine in the polymer complex and the iodine in the wound fluid in contact with the complex. Further release of available iodine from the polymer complex into the wound fluid is dependent on the rate of depletion of the iodine in the wound fluid which is in contact with the complex.

One starting polymer which can be used in the preparation of the iodine complexes of the present invention is crosslinked polyvinylpyrrolidone, which the National Formulary calls "Crospovidone" and which is commercially available from, e.g., the ISP Division of GAF Corporation as Polyplasdone® XL. This polymer is capable of strongly complexing with iodine to form a stable water-insoluble but water swellable complex upon iodination at ambient temperatures with an aqueous solution of elemental iodine and a soluble iodide salt in which the molar ratio of iodide ion to iodine exceeds 1 to 1. This iodination process yields the polymer-iodine complex of the present invention without adversely affecting the starting polymer. Antimicrobial activity on the wound surface results from diffusion controlled release of iodine from the complex to the wound surface. The crosslinked PVP iodine complex of the invention has a broad spectrum of antimicrobial activity characteristic of iodine and povidone-iodine and is not readily inactivated by wound fluids. Crosslinked povidone-iodine complexes of the present invention can be used in a number of topical antimicrobial products such as powders, aerosol sprays, gels, creams, ointments, and water sensitive films. The crosslinked PVP-iodine complexes of the present invention can also be used for other microbial infections of the skin such as athlete's foot.

DETAILED DESCRIPTION OF THE INVENTION

EXAMPLE 1

Figure 1:
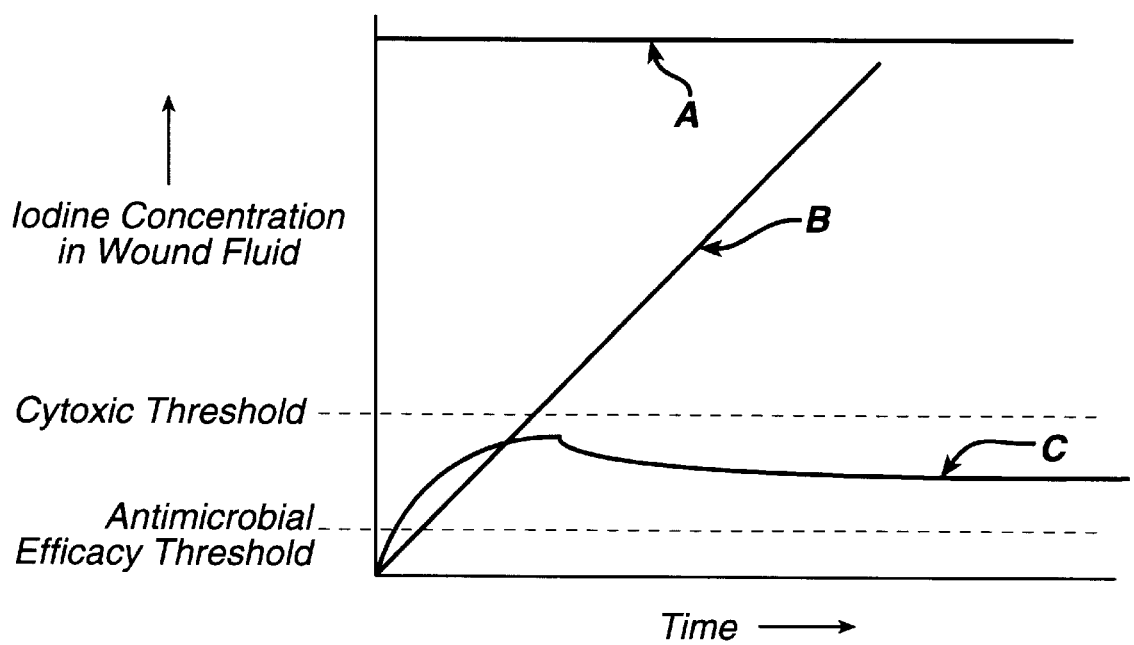
FIG. 1 is a conceptual comparison, in graphical form, of the iodine release characteristics as a function of time of a conventional povidone-iodine solution (A); a composition according to U.S. Pat. No. 5,242,985 (B); and a composition according to the present invention (C).

A crosslinked polyvinyl pyrrolidone-iodine complex according to the present invention was prepared from a water-insoluble, water-swellable crosslinked polyvinylpyrrolidone available from the ISP Division of GAF Corporation as Polyplasdone® XL.

Polyplasdone® XL is a water-insoluble, water-swellable synthetic crosslinked homopolymer of N-vinyl-2-pyrrolidone. It contains not less than 11.0 percent and not more than 12.8 percent of Nitrogen (N), calculated in the anhydrous basis, and meets the standards set for Crospovidone in National Formulary, Edition No. 18. "crospovidone" is the name which the National Formulary uses for crosslinked homopolymers of 1-vinyl-2pyrrolidone. 1500 grams of water were mixed with 1433 grams of an aqueous iodinating solution containing 1.27% by weight iodine ($I_2$) and 3.0% by weight sodium iodide in a 4 liter beaker. The iodinating solution was 0.05 M with respect to iodine and 0.2 M with respect to iodide ion, so that the molar ratio of iodide ion to iodine was 4:1. 120.8 grams of Polyplasdone® XL were added with stirring to the contents of the beaker at room temperature. The resulting mixture was vigorously stirred for 5 minutes during which time the crosslinked povidone-iodine complex was formed. The crosslinked polyvinylpyrrolidine-iodine complex was recovered in moist form with the use of a vacuum filtration unit. After rinsing with a small amount of water, the moist filter cake was dried overnight at 55° C.±5° C., crushed to a free-flowing powder and further dried at 55° C.±5° C. to a constant weight. Available iodine content of the crosslinked povidone-iodine complex was measured by dispersing an accurately weighed amount of the complex in a large excess of iodine-free solution containing approximately 5% by weight of potassium iodide and titrating it with 0.02 Normal sodium thiosulfate. The complex was found to contain 17% available iodine. The available iodine content of crosslinked povidone-iodine complexes in accordance with the invention can be varied by changing the concentration of iodine in the iodinating solution and by changing the ratio of the amount of the starting polymer to the amount of the iodinating solution.

It will be understood that other water soluble iodide salts such as potassium iodide and ammonium iodide can be used in place of sodium iodide in the iodinating solution. In all cases, the molar ratio of iodide to iodine in the iodinating solution must be in excess of 1 to 1. Molar ratios of iodide ion to iodine in excess of 3 to 2 are preferred and molar ratios in excess of 3 to 1 are most preferred.

Antimicrobially effective, non-irritating crosslinked polyvinylpyrrolidone-iodine complexes of the present invention may have available iodine contents ranging from about 0.2% by weight to about 50% by weight. Preferably, the available iodine content ranges from about 2% by weight to about 30% by weight and even more preferably, from about 8% by weight to about 20% by weight.

EXAMPLES 2–6

Additional crosslinked polyvinylpyrrolidone-iodine complexes of the present invention were made according to the method described in Example 1 above. The amounts of crosslinked povidone ("povidone" is the pharmaceutical industry's nomenclature for polyvinylpyrrolidone), water, and iodinating solution for each different sample are shown in Table I. Also shown in Table I are the molarities of the iodinating solution as well as the available iodine content for each sample.

TABLE I

| | | Iodinating solution | | | Cross-linked Povidone grams | Available iodine content |
|---|---|---|---|---|---|---|
| | | | Molarity | | | |
| | Water, grams | Amount, grams | Iodine, $I_2$ | Iodide, ion | | |
| Example 2 | 300 | 300 | 0.05 M | 0.2 M | 48.16 | 8.3% |
| Example 3 | 250 | 50 | 0.05 M | 0.1 M | 19.13 | 4.5% |
| Example 4 | 445 | 94.56 | 0.05 M | 0.2 M | 60 | 2.18% |
| Example 5 | 493 | 47.28 | 0.05 M | 0.2 M | 60 | 1.07% |
| Example 6 | 516 | 23.64 | 0.05 M | 0.2 M | 60 | 0.50% |

The data presented herein for Examples 1 through 6 reflect experimental conditions and analytical results.

Crosslinked polyvinylpyrrolidone-iodine complexes of the present invention may also be made by a fluidized bed process in which the crosslinked povidone polymer particles are suspended in a gaseous stream into which the iodinating solution is injected and allowed to react with the polymeric material.

EXAMPLE 7

An antimicrobial powder was prepared by mixing 89.895 grams of the crosslinked povidone-iodine complex (in powder form) made according to Example 1 with 5 mg. of Aerosol OTB® (Sodium dioctyl sulfosuccinate/sodium benzoate), 100 mg of Cab-O-Sil M-5® (a fumed silica powder) and 10 grams of Natrosol 250H® (hydroxyethyl cellulose screened through 60 mesh) in a wide mouth cylindrical glass jar. The mixed materials were then blended for 5 minutes on a roller blender to yield a free-flowing antiseptic powder. This powder can be sprinkled on a wound site as an antiseptic and to promote wound healing.

Sodium dioctyl sulfosuccinate/sodium benzoate a non-irritating surfactant, enhances the wetting of the crosporidone-iodine complex by the wound fluid and permits the release of iodine into the wound fluid. Concentrations of the sodium dioctyl sulfosuccinate/sodium benzoate range from 1 ppm to 5% by weight. The preferred range is 10 ppm to 1% by weight of the antimicrobial powder and the most preferred range is 20 to 200 ppm by weight of the antimicrobial powder.

Cab-O-Sil M-5® (fumed silica) serves to improve the flow characteristics of the powder to ensure ease and uniformity of application. Concentrations of Cab-O-Sil M-5® from 0.0001% w/w to 2% w/w may be used. The preferred range is from 0.001% w/w to 0.5% w/w and more preferred range is from 0.005% w/w to 0.2% w/w. Other flow additives including precipitated silica and dicalcium phosphate may be used in place of fumed silica.

A hydrophilic polymer like Natrosol 250 H (hydroxyethyl cellulose) improves the consistency of the crosslinked povidone-iodine applied to the wound by making it more cohesive, softer in consistency and by helping keep it moist on the wound surface. Concentrations of the hydrophilic polymer up to 75% w/w may be used. The preferred range is between 4% to 40% w/w and the most preferred range is from 8% w/w to 20% w/w.

EXAMPLE 8

An antimicrobial powder was prepared using the procedure described in Example 7. The Example 8 powder had the following composition: 89.9 grams of the crosslinked povidone-iodine complex of Example 2; 5 mg. of Aerosol® OTB; 100 mg. of Cab-O-Sil M-5® ; and 10 grams of Natrosol 250 H. As can be seen by reference to Table I, the available iodine content of the Example 2 complex was 7.5%.

EXAMPLE 9

An antimicrobial gel dispersion containing 11.4 grams of the crosslinked povidone-iodine complex of Example 1, 200 grams of propylene glycol, 1 gram methyl paraben, 10 grams of Carbopol-974P NF; 1 gram NaOH, and 776.6 grams of water was prepared. The methyl paraben and the Carbopol-974P NF were dispersed in the propylene glycol by mixing for 20 minutes. 450 grams of water were then added to the dispersion and mixing was continued for 30 minutes until a uniform dispersion was obtained. The 11.4 grams of the complex of Example 1 were gradually added, with stirring, to the dispersion and stirring was continued for 30 minutes. The pH was adjusted by adding 250 mls. of 0.1 N NaOH solution. The remaining water was added to adjust the final weight to 1000 grams and stirring was continued for thirty minutes. The final pH was approximately 5.0. As mentioned earlier herein, the available iodine content of the complex of Example 1 was 17%. The available iodine content of the antimicrobial gel dispersion of this Example 9 was 0.2% by weight.

The crossliked polyvinylpyrrolidone-iodine complex of Example 2, the antimicrobial powders of Examples 7 and 8, and the gel dispersion of Example 9 were microbiologically tested using a modification of test methodology described in the FDA/OTC Tentative Final Monograph for First Aid Antiseptic Drug Products and were found effective against all three specified test micro-organisms. The test requires at least 99.9% reductions in the viable counts of *Staph. aureus* (ATCC 6538), *Pseudomonas aerug.* (ATCC 9027) and *Escherichia coli* (ATCC 8739) after contact for 10 minutes in presence of serum. The results of this test demonstrate that the Example 2 complex and the Example 7, 8 and 9 preparations are antiseptically effective.

The antimicrobial powders of Examples 7 and 8 and the gel dispersion of Example 9 were also tested to assess their wound irritation and wound healing characteristics. The testing was conducted as follows:

Preparation of animals: The tests were conducted on six to eight weaned, female crossbred swine. On day-0, the animals were anesthetized by inhalation of isofluorane. The skin was prepared by clipping the hair followed by shaving the remainder with a razor. The surgical field (paravertebral areas) was washed with an antimicrobial soap, rinsed with water and finally washed with alcohol. Proper aseptic technique was followed to minimize potential for exogenous infection.

Preparation of wounds: On the prepared site, 20 to 30 partial thickness wounds were made on the right and on the left paravertebral areas using a Castro-Viejo dermatome with wound dimensions of approximately 1 cm×1 cm×0.5 mm.

The wounds formed four quadrants of 10 to 14 wounds each. Wound treatments were assigned to each quadrant and rotated through the four quadrants using a latin square design so that each treatment would be at the same quadrant on two animals.

Following hemostasis, the antimicrobial preparations of Examples 7, 8 and 9 were applied to the wounds in each quadrant according to the predetermined format. The wounds were covered with adhesive bandages which were changed daily. The test procedure utilized the following controls: adhesive bandage (A), a commercially available antiseptic liquid containing 0.13% benzalkonium chloride (B), a commercially available water soluble ointment containing 1% povidone-iodine (C). The preparations to be tested were applied on two consecutive days (day 0 as well as on day 1). Only adhesive bandages on the wounds were changed on days 2, 3 and 4.

Observations and evaluations: None of the wounds observed on a daily basis for five days following treatment showed inflammation, edema, infection or skin maceration. On day 5, following the evaluation, a representative sample was biopsied and the remaining wounds and the surrounding skin are surgically excised. The skin strips were incubated in 0.5 M NaBr solution for 24 hours at 37° C. to facilitate separation of dermis from epidermis. Wound epithelialization was measured after separating the dermis from epidermis. The percentage of wounds completely epithelialized was calculated and compared with other treatments in the study. The results are shown below.

|  | Control A | Control B | Control C | Ex. 7 | Ex. 8 | Ex. 9 |
|---|---|---|---|---|---|---|
| Wounds Healed: | 10% | 0% | 4% | 77% | 61% | 16% |

As can be seen, the antimicrobial preparations of Examples 7, 8 and 9 provided faster wound epithelialization than any of the controls.

EXAMPLE 10

A water dispersible polymeric film containing the crosslinked povidone-iodine complex of Example 1 was prepared as follows. 40 grams of the complex of Example 1 were thoroughly blended with 20 grams of Carbowax 8000 (a commercially available polyethylene glycol), 20 grams of Polyox WSR N-80 (also a commercially available polyethylene glycol) and 20 grams of Methocel A-15C (a commercially available methyl cellulose). The blended materials were pressed between hot metal plates at 100° C. to form a thermoplastic film. This film can be used as an antiseptic patch either alone or in combination with an adhesive pad or absorbent dressing.

Although the examples described above are intended to illustrate the breadth of utility for the invention, they should not be viewed as limitations on the invention. Numerous additional applications, particularly in the field of wound care and skin care should be obvious to those skilled in the art.

FIG. 1 is a conceptual comparison, in graphical form, of the iodine release characteristics as a function of time of a conventional povidone-iodine solution (A); a composition according to U.S. Pat. No. 5,242,985 (B); and a composition according to the present invention (C). It will be understood that it is virtually impossible to measure the concentration of iodine at the interface of a wound surface and a iodine-containing material, such as A, B or C, which has been applied to the wound. However, the concentration of iodine in wound fluid which results from the application of a conventional povidone-iodine solution (A) is, from the outset of application of the solution to the wound, considerably in excess of the Cytotoxic Threshold. This results in wound irritation and retardation of wound healing. The concentration of iodine in wound fluid which results from the application of a composition disclosed in U.S. Pat. No. 5,242,985 is below the Antimicrobial Efficacy Threshold immediately upon application of the composition to the wound. After a period of time, the concentration of iodine exceeds the Antimicrobial Efficacy Threshold and is below the Cytotoxic Threshold. After the further passage of time, the concentration of iodine increases and eventually exceeds the Cytotoxic Threshold. This can be expected to likewise result in wound irritation and retardation of wound healing. As mentioned earlier, the release of iodine from compositions of the present invention is equilibrium controlled. Accordingly, the concentration of iodine in a wound fluid which results from the application of the crosslinked polyvinylpyrrolidone-iodine complex of the present invention reaches, shortly after application, concentration levels which are above the Antimicrobial Efficacy Threshold and below the Cytotoxic Threshold. This means that compositions according to the present invention are antimicrobially effective but do not irritate the wound or retard wound healing.

What is claimed is:

1. A water-insoluble, water-swellable antimicrobial complex which avoids wound irritation and retardation of wound healing comprising crosslinked polyvinylpyrrolidone and iodine, said complex being adapted to release iodine by an equilibrium controlled diffusion process when in contact with a wound.

2. The complex of claim 1 having an available iodine content of from about 0.5% by weight to about 50% by weight.

3. The complex of claim 1 having an available iodine content of from about 2% by weight to about 30% by weight.

4. The complex of claim 1 having an available iodine content of from about 8% by weight to about 20% by weight.

5. An antimicrobial complex which avoids wound irritation and retardation of wound healing comprising crosslinked polyvinylpyrrolidone-iodine complex made by a method which comprises:

A) providing an aqueous iodination solution comprising iodine and, iodide ion, the molar ration of said iodide ion to iodine in said solution being in excess of 1:1.

B) adding cross linked polyvinylpyrrolidone to said iodinating solution; and

C) reacting said crosslinked polvvinylpyrrolidone with said iodinating solution at ambient temperature.

6. The water-insoluble, water-swellable antimicrobial complex of claim 1 wherein said complex promotes wound healing.

* * * * *